United States Patent
Jung et al.

(10) Patent No.: US 10,408,817 B2
(45) Date of Patent: Sep. 10, 2019

(54) KIT FOR DIAGNOSIS OF CORONARY HEART DISEASE USING MULTI-METABOLITES AND CLINICAL PARAMETERS, AND METHOD FOR DIAGNOSIS OF CORONARY HEART DISEASE USING THE SAME

(71) Applicant: KOREA INSTITUTE OF SCIENCE AND TECHNOLOGY, Seoul (KR)

(72) Inventors: Byung Hwa Jung, Seoul (KR); Jong Min Choi, Seoul (KR); Hong Seog Seo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/601,262

(22) Filed: May 22, 2017

(65) Prior Publication Data
US 2018/0156774 A1    Jun. 7, 2018

(30) Foreign Application Priority Data
Dec. 5, 2016 (KR) .................. 10-2016-0164459

(51) Int. Cl.
G01N 33/49 (2006.01)
(52) U.S. Cl.
CPC ..... *G01N 33/492* (2013.01); *G01N 2800/324* (2013.01); *G01N 2800/50* (2013.01); *G01N 2800/60* (2013.01)
(58) Field of Classification Search
CPC ............. G01N 33/492; G01N 2800/60; G01N 2800/324; G01N 2800/50
See application file for complete search history.

(56) References Cited

U.S. PATENT DOCUMENTS

| | | | |
|---|---|---|---|
| 8,137,977 B2 | 3/2012 | Kaddurah-Daouk et al. | |
| 9,134,322 B2 | 9/2015 | Body | |
| 9,140,703 B2 | 9/2015 | Hazen et al. | |
| 9,274,126 B2 | 3/2016 | Adourian et al. | |
| 9,354,222 B2 | 5/2016 | Jung et al. | |
| 2009/0208986 A1 | 8/2009 | Cho et al. | |
| 2016/0305931 A1 | 10/2016 | Jung et al. | |

FOREIGN PATENT DOCUMENTS

| | | |
|---|---|---|
| JP | 2014-532886 A | 12/2014 |
| KR | 10-1051470 B1 | 7/2011 |
| KR | 10-2012-0130164 A | 11/2012 |
| KR | 10-2016-0086730 A | 7/2016 |
| KR | 10-1660328 B1 | 9/2016 |
| KR | 10-2016-0123859 A | 10/2016 |
| WO | WO 2011/063032 A1 | 5/2011 |
| WO | WO 2013/068374 A2 | 5/2013 |

OTHER PUBLICATIONS

Lv et al. Metabolomic study of myocardial ischemia and intervention effects of Compound Danshen Tablets in rats using ultra-performance liquid chromatography/quadrupole time-of-flight mass spectrometry. Journal of Pharmaceutical and Biomedical Analysis 52 (2010) 129-135. (Year: 2010).*
Cheng et al. Metabolic Disturbances Identified in Plasma Are Associated With Outcomes in Patients With Heart Failure. (J Am Coll Cardiol Apr. 2015;65:1509-20. (Year: 2015).*
Pai et al. Hemoglobin A1c Is Associated With Increased Risk of Incident Coronary Heart Disease Among Apparently Healthy, Nondiabetic Men and Women. J Am Heart Assoc. 2013;2:e000077, 8 pages. (Year: 2013).*
Madjid et al. Components of the Complete Blood Count as Risk Predictors for Coronary Heart Disease. Tex Heart Inst J 2013;40(1): 17-29. (Year: 2013).*
Milane et al. Association of hypertension with coronary artery disease onset in the Lebanese population. SpringerPlus 2014, 3:533, 7 pages. (Year: 2014).*
Ozaki et al., "Circulating CD14+CD16+ Monocyte Subsets as Biomarkers of the Severity of Coronary Artery Disease in Patients With Stable Angina Pectoris", Circulation Journal, vol. 76, Oct. 2012, pp. 2412-2418.
Park et al., "Alteration in Metabolic Signature and Lipid Metabolism in Patients with Angina Pectoris and Myocardial Infarction", PLOS ONE, DOI:10.1371/journal. pone.0135228, Aug. 10, 2015, 15 pgs.
Arbel et al., "Admission glucose, fasting glucose, HbA1c levels and the SYNTAX score in non-diabetic patients undergoing coronary angiography," Clin. Res. Cardiol. (2014), vol. 103, pp. 223-227.

* cited by examiner

*Primary Examiner* — Sean C. Barron

(74) *Attorney, Agent, or Firm* — Birch, Stewart, Kolasch & Birch, LLP

(57) ABSTRACT

The present disclosure relates to a method and a diagnostic kit for diagnosing stable angina and acute myocardial infarction early through simple blood testing and checking of clinical parameters. Unlike conventional diagnostic methods, stable angina can be diagnosed as distinguished from acute myocardial infarction according to the present disclosure by using one diagnostic platform based on the change in the in-vivo levels of biological metabolites having different metabolic pathways and clinical parameters as well as medications affecting the onset and progress of the disease through multivariable analysis.

1 Claim, No Drawings

KIT FOR DIAGNOSIS OF CORONARY HEART DISEASE USING MULTI-METABOLITES AND CLINICAL PARAMETERS, AND METHOD FOR DIAGNOSIS OF CORONARY HEART DISEASE USING THE SAME

CROSS-REFERENCE TO RELATED APPLICATION

This application claims priority to Korean Patent Application No. 10-2016-0164459, filed on Dec. 5, 2016, and all the benefits accruing therefrom under 35 U.S.C. § 119, the contents of which in its entirety are herein incorporated by reference.

BACKGROUND

1. Field

The present disclosure relates to a method and a kit for diagnosis of stable angina and acute myocardial infarction using metabolites and clinical parameters of a patient.

DESCRIPTION OF GOVERNMENT-SUPPORTED RESEARCH AND DEVELOPMENT

This research was conducted by the Korea Institute of Science and Technology with support from the Creative Allied Project (CAP) of the Ministry of Science, ICT and Future Planning (sponsored by: National Research Council of Science & Technology, project name: Research on regulation of phosphorylation signaling system in vivo based on NBIT fusion technology, project number: CAP-12-01-KIST).

This research was also conducted by the Korea Institute of Science and Technology with support from the Traditional Natural Product-Based Genetic Donguibogam Project of the Ministry of Science, ICT and Future Planning (sponsored by: National Research Foundation of Korea, project name: Metabolomics-based standardization of MC interaction of traditional natural products, project number: NRF-2013M3A9C4078145).

2. Description of the Related Art

Cardiovascular disease (CVD) is a disease with the highest mortality in the world. According to a report by the World Health Organization (WHO), it is predicted that 23.6 million people will die of cardiovascular disease until 2030.

Coronary heart disease shows symptoms of angina, including stable angina (angina pectoris), unstable angina and myocardial infarction.

Among them, myocardial infarction, which is the number one cause of sudden death in adults, is increasing consistently. This disease is characterized by an imbalance in oxygen supply to the heart muscle due to blockage of a coronary artery and irreversible damage to myocardial cells. Unlike stable angina (angina pectoris) which can be pregnosed with repetitive and characteristic exertional chest pain, myocardial infarction shows abrupt thrombotic occlusion of coronary artery caused by rupture of vulnerable plaques. The vulnerable plaques have been diagnosed only by an invasive method using, e.g., intravascular ultrasound (IVUS) and early diagnosis is difficult because there is no biomarker that allows prediction and diagnosis before the disease breaks out.

Although stable angina (SA) on exertion is one of the most frequent initial clinical presentations of coronary heart disease (CHD), the search for specific risk factors has so far received little attention. In particular, plaque rupture and subsequent thrombosis formation are thought to trigger the occurrence of acute coronary syndrome (ACS) including unstable angina (UA) and myocardial infarction (MI), but not stable angina. This suggests that acute coronary syndrome (ACS) and stable angina (SA) may not share all the same risk factors.

For stable angina (SA), it is reported that, whereas the improvement of lifestyles and adequate drug therapy show no significant difference in mortality and occurrence of myocardial infarction as compared to coronary artery intervention performed at an early stage, an adequate drug therapy performed at an early stage can increase the survivability of patients. Therefore, diagnosis for preventive treatment of stable angina (SA) is very necessary.

There exist some biomarkers for acute coronary syndrome (ACS) such as myocyte necrosis, inflammation, vascular damage, hemodynamic stress, etc. However, for stable angina (SA), biomarkers for diagnosing disease are relatively insufficient although it is reported that a set of circulating CD14+ and CD16+ monocytes aggravates coronary heart disease in patients with stable angina (SA) (*Circ. J.* 2012; 76: 2412-2418).

At present, glutamic oxaloacetic transaminase (GOT), lactate dehydrogenase (LDH), creatine kinase-MB (CK-MB), troponin I, troponin T, C-reactive protein (CRP) and B-type natriuretic peptide (BNP) are also used as biomarkers for diagnosis of cardiovascular disease or heart failure. However, they are not biomarkers specific only for myocardial infarction or they can be diagnosed only after the onset of myocardial infarction. In addition, no diagnostic biomarker using low-molecular-weight metabolites found in blood is known yet.

REFERENCES OF THE RELATED ART

Non-Patent Document

*Circ. J.* 2012; 76: 2412-2418.

SUMMARY

The present disclosure is directed to providing a multi-biomarker platform for diagnosis of coronary heart disease (CHD), stable angina and myocardial infarction, based on the analysis of the in-vivo levels of biological metabolites specific for the diseases and the analysis of the correlation with clinical parameters.

In an aspect, the present disclosure provides a method for diagnosis of coronary heart disease (CHD), which includes: a step of analyzing the levels of metabolites and clinical parameters contained in a blood sample of a subject, wherein the metabolites include tryptophan, homoserine, fatty acid (18:0) (FA_18_0), fatty acid (22:6) (FA_22_6), lysophosphatidylcholine (lysoPC) (16:0) (LPC_16_0), lysoPC (18:0) (LPC_18_0), lysoPC (20:4) (LPC_20_4), lysoPC (22:6) (LPC_22_6) and phosphatidylcholine (PC) (34:2) (PC_34_2) and the clinical parameters include a white blood cell (WBC), a C-reactive protein (CRP), cholesterol, glucose and hemoglobin A1c (HbA1c); and a step of checking the presence of hypertension (HTN) and medication of statin of the subject.

In another aspect, the present disclosure provides a kit for diagnosis of coronary heart disease (CHD), which contains: a blood level measuring unit for measuring metabolites including tryptophan, homoserine, fatty acid (18:0) (FA_18_0), fatty acid (22:6) (FA_22_6), lysophosphatidylcholine (lysoPC) (16:0) (LPC_16_0), lysoPC (18:0) (LPC_18_0), lysoPC (20:4) (LPC_20_4), lysoPC (22:6) (LPC_22_6) and phosphatidylcholine (PC) (34:2) (PC_34_2) and clinical parameters including a white blood cell (WBC), a C-reactive protein (CRP), cholesterol, glucose and hemoglobin A1c (HbA1c), and a questionnaire for checking the presence of hypertension (HTN) and medication of statin.

According to the present disclosure, stable angina and myocardial infarction can be diagnosed early through simple blood testing and checking of clinical parameters.

Specifically, they can be diagnosed easily because in-vivo metabolites such as amino acids or lipids and the result of blood tests commonly carried out by clinical institutes such as hospitals are used as biomarkers. Because the levels of the biological metabolites and clinical parameters according to the present disclosure in vivo, e.g., in blood, are increased or decreased specifically in a subject with coronary heart disease such as myocardial infarction and angina, the coronary heart disease can be diagnosed conveniently and accurately by systematically comparing and analyzing the in-vivo levels.

Also, unlike the existing diagnostic method of diagnosing a disease using a single biomarker, stable angina can be diagnosed as distinguished from acute myocardial infarction using one diagnostic platform based on the change in the in-vivo levels of biological metabolites having different metabolic pathways and clinical parameters affecting the onset and progress of the disease as well as medications through multivariable analysis.

Accordingly, unlike the existing biomarker which allows for diagnosis of myocardial infarction based on myocyte necrosis only, the multi-biological metabolite marker diagnostic platform according to the present disclosure allows for prediction and early diagnosis of not only acute myocardial infarction but also stable angina before the onset of myocardial infarction as well as prognosis, treatment and prevention of the disease through a simple test.

DETAILED DESCRIPTION

Hereinafter, the present disclosure is described in detail.

In an exemplary embodiment, the present disclosure provides a method for providing basic information for diagnosis of coronary heart disease (CHD) or a method for diagnosis thereof, which includes: a step of analyzing the levels of metabolites and clinical parameters contained in a blood sample of a subject, wherein the metabolites include tryptophan, homoserine, fatty acid (18:0) (FA_18_0), fatty acid (22:6) (FA_22_6), lysophosphatidylcholine (lysoPC) (16:0) (LPC_16_0), lysoPC (18:0) (LPC_18_0), lysoPC (20:4) (LPC_20_4), lysoPC (22:6) (LPC_22_6) and phosphatidylcholine (PC) (34:2) (PC_34_2) and the clinical parameters include a white blood cell (WBC), a C-reactive protein (CRP), cholesterol, glucose and hemoglobin A1c (HbA1c); and a step of checking the presence of hypertension (HTN) and medication of statin of the subject.

In an exemplary embodiment, the coronary heart disease may include stable angina (SA) and acute myocardial infarction (AMI).

An exemplary embodiment according to the present disclosure may further include a step of predicting stable angina (SA) and acute myocardial infarction (AMI) by substituting the blood levels of the metabolites and clinical parameters contained in the blood sample, the presence of hypertension and the medication of statin in Equation 1 or 2.

Probability of onset of stable angina (SA), [Equation 1]
$$P_{sa} = \pi_1(\chi) = \frac{\exp(\alpha_1 + \beta'_1\chi)}{1 + \exp(\alpha_1 + \beta'_1\chi) + \exp(\alpha_2 + \beta'_2\chi) + \exp(\alpha_3 + \beta'_3\chi)}$$

Probability of onset of acute myocardial infarction (AMI), [Equation 2]
$$P_{ami} = \pi_3(\chi) = \frac{\exp(\alpha_3 + \beta'_3\chi)}{1 + \exp(\alpha_1 + \beta'_1\chi) + \exp(\alpha_2 + \beta'_2\chi) + \exp(\alpha_3 + \beta'_3\chi)}$$

In Equations 1 and 2,
$\alpha_1 = -5.1033$,
$\alpha_2 = -7.2726$,
$\alpha_3 = -16.5253$,
$\beta'_{1\chi} = 3.233*HTN+3.016*statin+0.4336*WBC-0.0364*CRP-0.0189*cholesterol+0.0534*glucose-0.8651*HbA1c+0.0689*FA\_18\_0-0.00252*FA\_22\_6+0.0332*homoserine-0.0037*LPC\_16\_0+0.00318*LPC\_18\_0-0.0209*LPC\_20\_4+0.1109*LPC\_22\_6+0.0118*PC\_34\_2-0.0159*tryptophan$,
$\beta'_{2\chi} = 3.18*HTN+1.4578*statin+0.4631*WBC-0.00977*CRP-0.02*cholesterol+0.0127*glucose+0.0981*HbA1c+0.0349*FA\_18\_0-0.0173*FA\_22\_6+0.0564*homoserine+0.00993*LPC\_16\_0-0.0308*LPC\_18\_0-0.1525*LPC\_20\_4+0.2896*LPC\_22\_6+0.0239*PC\_34\_2+0.00366*tryptophan$,
$\beta'_{3\chi} = 3.9577*HTN-1.6837*statin+0.5634*WBC+0.0705*CRP-0.00031*cholesterol+0.0174*glucose+0.3797*HbA1c-0.00059*FA\_18\_0+0.00472*FA\_22\_6+0.6163*homoserine-0.00314*LPC\_16\_0-0.0438*LPC\_18\_0-0.0411*LPC\_20\_4+0.2548*LPC\_22\_6+0.0517*PC\_34\_2-0.2288*tryptophan$.

The unit of the blood levels of the clinical parameters of the subject substituted in Equation 1 or 2 are cell/mm$^3$ for the white blood cell (WBC), mg/L for the C-reactive protein (CRP), mg/dL for the cholesterol, mg/dL for the glucose and % for the hemoglobin A1c (HbA1c), and, for the presence of hypertension (HTN), 1 is substituted in Equation 1 or 2 when the systolic blood pressure of the subject is 140 mmHg or higher or the diastolic blood pressure is 90 mmHg or higher and 0 is substituted when the systolic blood pressure is below 140 mmHg and, for the medication of statin, 1 is substituted in Equation 1 or 2 when the subject takes statin and 0 is substituted when the subject does not take statin.

In an exemplary embodiment of the present disclosure, the step of analyzing the levels of metabolites contained in the blood sample of the subject may include: a step of performing mass spectrometry for the blood sample; a step of obtaining chromatograms and mass spectrometry data from the result of the mass spectrometry; and step of obtaining normalized peak areas by dividing the peak areas of the mass spectrometry data by the total peak areas of the chromatograms (normalization). The normalization is carried out to reduce data error by correcting the peak areas of the obtained mass spectrometry data with the total peak areas of the chromatograms. The normalized peak areas of the respective metabolites may be substituted in Equation 1 or 2.

In an exemplary embodiment of the present disclosure, the method may further include, before the step of analyzing the levels of metabolites and clinical parameters contained in the blood sample of the subject, a step of deproteinizing the blood sample by pretreating with methanol. Specifically, the pretreatment step may include a step of adding to the blood sample at room temperature 2-4 times the volume of cold methanol and mixing the same, a step of centrifuging the mixture and separating a supernatant and a step of diluting the supernatant by adding distilled water. In an exemplary embodiment, the blood sample may be a serum sample.

In an exemplary embodiment, the step of analyzing the levels of metabolites contained in the blood sample of the subject may include performing liquid chromatography-mass spectrometry. More specifically, the liquid chromatography-mass spectrometry may be ultra performance liquid chromatography-quadrupole time-of-flight mass spectrometry (UPLC-QTOF-MS).

In another exemplary embodiment, the present disclosure may provide a kit for diagnosis of coronary heart disease (CHD). The coronary heart disease includes stable angina (SA) and acute myocardial infarction (AMI).

In an exemplary embodiment, the kit may contain a blood level measuring unit for measuring metabolites including tryptophan, homoserine, fatty acid (18:0) (FA_18_0), fatty acid (22:6) (FA_22_6), lysophosphatidylcholine (lysoPC) (16:0) (LPC_16_0), lysoPC (18:0) (LPC_18_0), lysoPC (20:4) (LPC_20_4), lysoPC (22:6) (LPC_22_6) and phosphatidylcholine (PC) (34:2) (PC_34_2) and clinical parameters including a white blood cell (WBC), a C-reactive protein (CRP), cholesterol, glucose and hemoglobin A1c (HbA1c); and a questionnaire for checking the presence of hypertension (HTN) and medication of statin.

In an exemplary embodiment, the kit may further contain an instruction describing a method for predicting stable angina (SA) and acute myocardial infarction (AMI) by substituting the blood levels of metabolites and clinical parameters measured by the blood level measuring unit and the presence of hypertension (HTN) and medication of statin checked in the questionnaire in Equation 1 or 2.

Probability of onset of stable angina (SA), [Equation 1]

$$P_{sa} = \pi_1(\chi) = \frac{\exp(\alpha_1 + \beta'_1\chi)}{1 + \exp(\alpha_1 + \beta'_1\chi) + \exp(\alpha_2 + \beta'_2\chi) + \exp(\alpha_3 + \beta'_3\chi)}$$

Probability of onset of acute myocardial infarction (AMI), [Equation 2]

$$P_{ami} = \pi_3(\chi) = \frac{\exp(\alpha_3 + \beta'_3\chi)}{1 + \exp(\alpha_1 + \beta'_1\chi) + \exp(\alpha_2 + \beta'_2\chi) + \exp(\alpha_3 + \beta'_3\chi)}$$

In Equations 1 and 2,
$\alpha_1 = -5.1033$,
$\alpha_2 = -7.2726$,
$\alpha_3 = -16.5253$,
$\beta'_{1\chi} = 3.233*HTN + 3.016*statin + 0.4336*WBC - 0.0364*CRP - 0.0189*cholesterol + 0.0534*glucose - 0.8651*HbA1c + 0.0689*FA\_18\_0 - 0.00252*FA\_22\_6 + 0.0332*homoserine - 0.0037*LPC\_16\_0 + 0.00318*LPC\_18\_0 - 0.0209*LPC\_20\_4 + 0.1109*LPC\_22\_6 + 0.0118*PC\_34\_2 - 0.0159*tryptophan$,
$\beta'_{2\chi} = 3.18*HTN + 1.4578*statin + 0.4631*WBC - 0.00977*CRP - 0.02*cholesterol + 0.0127*glucose + 0.0981*HbA1c + 0.0349*FA\_18\_0 - 0.0173*FA\_22\_6 + 0.0564*homoserine + 0.00993*LPC\_16\_0 - 0.0308*LPC\_18\_0 - 0.1525*LPC\_20\_4 + 0.2896*LPC\_22\_6 + 0.0239*PC\_34\_2 + 0.00366*tryptophan$,
$\beta'_{3\chi} = 3.9577*HTN - 1.6837*statin + 0.5634*WBC + 0.0705*CRP - 0.00031*cholesterol + 0.0174*glucose + 0.3797*HbA1c - 0.00059*FA\_18\_0 + 0.00472*FA\_22\_6 + 0.6163*homoserine - 0.00314*LPC\_16\_0 - 0.0438*LPC\_18\_0 - 0.0411*LPC\_20\_4 + 0.2548*LPC\_22\_6 + 0.0517*PC\_34\_2 - 0.2288*tryptophan$.

The unit of the blood levels of the clinical parameters of the subject substituted in Equation 1 or 2 are cell/mm$^3$ for the white blood cell (WBC), mg/L for the C-reactive protein (CRP), mg/dL for the cholesterol, mg/dL for the glucose and % for the hemoglobin A1c (HbA1c), and, for the presence of hypertension (HTN), 1 is substituted in Equation 1 or 2 when the systolic blood pressure of the subject is 140 mmHg or higher or the diastolic blood pressure is 90 mmHg or higher and 0 is substituted when the systolic blood pressure is below 140 mmHg and, for the medication of statin, 1 is substituted in Equation 1 or 2 when the subject takes statin and 0 is substituted when the subject does not take statin.

In an exemplary embodiment, the instruction may contain, as a method for analyzing the blood levels of the metabolites measured by the blood level measuring unit: performing mass spectrometry for the blood sample; obtaining chromatograms and mass spectrometry data from the result of the mass spectrometry; and obtaining normalized peak areas by dividing the peak areas of the mass spectrometry data by the total peak areas of the chromatograms, and the normalized peak areas of the respective metabolites are substituted in Equation 1 or 2.

In an exemplary embodiment, the kit may further contain a mass spectrometer. The mass spectrometer may contain a liquid chromatography-mass spectrometer. More specifically, the liquid chromatography-mass spectrometer may be an ultra performance liquid chromatography-quadrupole time-of-flight mass spectrometer (UPLC-QTOF-MS).

In an exemplary embodiment, the kit may further contain methanol and a centrifuge for deproteinizing the blood sample with methanol.

Hereinafter, the present disclosure will be described in detail through examples. However, the following examples are for illustrative purposes only and it will be apparent to those of ordinary skill in the art that the scope of the present disclosure is not limited by the examples.

Example

As an exemplary embodiment of the present disclosure, it was confirmed through the following experiment that information for diagnosis of acute myocardial infarction and stable angina may be provided or the same can be predicted based on the blood levels of the metabolites tryptophan, homoserine, fatty acid (fatty acid) (18:0), fatty acid (22:6), lysoPC (lysophosphatidylcholine) (16:0), lysoPC (18:0), lysoPC (20:4), lysoPC (22:6) and PC (Phosphatidylcholine) (34:2) and the clinical parameters white blood cell (WBC), C-reactive protein (CRP), cholesterol, glucose and hemoglobin A1c (HbA1c), the presence of hypertension and medication of statin.

1. Selection of Test Subjects

A normal control group with no cardiovascular disease (control) and patients with stable angina (SA), unstable angina (UA) and acute myocardial infarction (AMI) were recruited as test subjects from Korea University Guro Hospital (Seoul, Korea). The coronary artery patient group consisted of 107 patients with stable angina, 45 patients with unstable angina and 56 patients with acute myocardial infarction and the normal control group consisted of healthy 101 men and women. The age and the presence of hypertension of the control group and the patient groups, the number of the patients with diabetes and hyperlipidemia, the number of those who take statin or smoke (% for each group) and the medians (first quantile and third quantile) of biomarkers for each group are shown in Table 1.

The biological metabolites contained in the serum samples were separated according to their retention times as the samples passed through the ultra performance liquid chromatography (UPLC) system and detected according to their mass-to-charge ratios as they passed through the Synapt G2 MS system. Specifically, an ACQUITY BEH $C_{18}$ column (2.1×100 mm, 1.7 μm) was used for the UPLC system and the column temperature and the autosampler temperature were set to 50° C. and 4° C., respectively. As mobile phases, distilled water containing 0.1% formic acid (mobile phase A) and methanol containing 0.1% formic acid

TABLE 1

|  | 1. Control | 2. SA | 3. UA | 4. AMI |
|---|---|---|---|---|
| Subjects | 101 | 107 | 45 | 56 |
| Number (%) of males | 40 (39.6) | 57 (53.3) | 23 (51.1) | 44 (78.6) |
| Number (%) of patients with hypertension | 6 (5.9) | 52 (48.6) | 22 (48.9) | 30 (53.6) |
| Number (%) of patients with diabetes | 4 (4) | 23 (21.5) | 11 (24.4) | 13 (23.2) |
| Number (%) of patients with hyperlipidemia | 0 (0) | 6 (5.6) | 3 (6.7) | 3 (5.4) |
| Number (%) of statin takers | 12 (11.9) | 43 (40.2) | 14 (31.1) | 14 (25) |
| Number (%) of smokers | 17 (16.8) | 34 (31.8) | 12 (26.7) | 30 (53.6) |
| Age | 55 (50, 63) | 61 (54, 69) | 63 (56, 70) | 61 (54, 66.5) |
| BMI: $Kg/m^2$ (first quantile, third quantile) | 23.1 (21.4, 25.5) | 24.4 (22.3, 26.2) | 24.4 (22.8, 26.3) | 24.3 (21.8, 26.2) |
| Systolic blood pressure (mmHg) | 125 (115, 135) | 125 (117, 134) | 123 (117, 130) | 119.5 (105, 129.5) |
| Diastolic blood pressure (mmHg) | 79 (73, 88) | 77 (68, 82) | 75 (67, 83) | 72 (65, 80) |
| Pulse rate (neat/min) | 75 (69, 82) | 70 (61, 77) | 70 (62, 79) | 71 (64.5, 84) |
| White blood cell ($cell/mm^3$) | 5.6 (4.5, 6.8) | 6.2 (5.1, 7.6) | 6.4 (5.3, 7.3) | 6.8 (5.6, 8.1) |
| CRP (C-reactive protein, mg/L) | 0.5 (0.2, 1.6) | 0.8 (0.4, 1.2) | 0.8 (0.4, 1.9) | 1.1 (0.5, 2.4) |
| Cholesterol (mg/dL) | 198 (176, 222) | 169 (139, 206) | 181 (145, 194) | 167 (138.5, 199) |
| HDL (mg/dL) | 57 (46, 67) | 50 (43, 57) | 45 (39, 52) | 43 (37, 52.5) |
| LDL (mg/dL) | 122 (108, 138) | 99 (73, 137) | 109 (84, 123) | 90 (78.5, 115.5) |
| Triglyceride (mg/dL) | 110 (82, 142) | 121 (82, 160) | 129 (85, 173) | 132.5 (81.5, 167) |
| AST (IU/L) | 22 (18, 26) | 22 (19, 27) | 20 (16, 31) | 24 (18, 35.5) |
| ALT (IU/L) | 19 (14,26) | 20 (15, 28) | 21 (13, 32) | 20 (16, 31) |
| Glucose (mg/dL) | 95 (89, 104) | 99 (91, 108) | 96 (88, 107) | 99.5 (91, 119.5) |
| BUN (mg/dL) | 13.8 (11.5, 16.5) | 14 (12.6, 16.6) | 14.1 (13.4, 18.1) | 14.3 (11.8, 16.5) |
| Creatinine (mg/dL) | 0.8 (0.7, 0.9) | 0.9 (0.8, 1) | 0.9 (0.6, 1) | 1 (0.8, 1.1) |
| HbA1c (%) | 5.3 (4.9, 5.9) | 5.1 (4.3, 5.9) | 5.7 (5, 6.3) | 5.8 (5.4, 6.3) |

Categorical variables are indicated by number (%) and continuous variables are indicated by medians (first quantile, third quantile).

2. Preparation of Serum Samples

Serum samples were obtained by centrifuging venous blood obtained from the patient groups and the normal control group. All the serum samples were stored at −80° C. prior to analysis. Then, the serum samples were deproteinized by pretreating with methanol. The serum samples were heated to room temperature and completely mixed after adding 3 times the volume of ice-cold methanol. After performing centrifugation, a predetermined amount of a supernatant was collected and diluted by adding half (½) the volume of distilled water.

3. Analysis of Biological Metabolites Through Ultra Performance Liquid Chromatography-Quadrupole Time-of-Flight Mass Spectrometry (UPLC-QTOF-MS)

The pretreated serum samples of the patient groups and the normal control group were analyzed by ultra performance liquid chromatography-quadrupole time-of-flight mass spectrometry (UPLC-QTOF-MS; ACQUITY UPLC system, Synapt G2 MS system, Waters).

(mobile phase B) were used. UPLC was performed by gradient elution by flowing the two mobile phases into the UPLC system while varying their ratios with analysis time. The order of injected was randomized to preclude any tendency resulting therefrom. The biological metabolites contained in the serum samples were detected in the Synapt G2 system in the positive and negative ionization modes of the mass spectrometer and analyzed in the $MS^E$ mode.

A detailed analysis condition of the Synapt G2 system is as follows.

TABLE 2

| Acquisition mode | ESI (+/−) mode |
|---|---|
| Capillary voltage | (+) 3.2 kV/(−) 2.5 kV |
| Sample cone voltage | 40 V |
| Source temperature | 120° C. |
| Desolvation temperature | 350° C. |
| Cone gas flow rate | 100 L/h |
| Desolvation gas flow rate | 800 L/h |

Specifically, analysis was performed with the capillary voltage set to (+) 3.2 kV in the positive ionization mode and to (−) 2.5 kV in the negative ionization mode and the cone voltage set to 40 V using the electrospray ionization (ESI) method. The source temperature and the desolvation temperature were set to 120° C. and 350° C., respectively, and the cone gas flow rate and the desolvation gas flow rate were set to 100 L/h and 800 L/h, respectively. From the serum analysis result by ultra performance liquid chromatography-quadrupole time-of-flight mass spectrometry (UPLC-QTOF-MS), chromatograms and mass spectrometry data were obtained.

4. Analysis of Biological Metabolites in Serum Samples from Coronary Artery Patient Groups and Normal Control Group The chromatogram and spectrum data of the metabolites in the serum samples from the stable angina, unstable angina and myocardial infarction patient groups and the normal control group were deconvoluted using the MassLynx™ (Mass Spectrometry Software, Waters) and MarkerLynx™ (Waters) programs to obtain candidate metabolite markers. The peak area of each marker candidate was normalized by the total peak area of the chromatogram.

The medians (first quantile, third quantile) normalized by the peak areas are given in Table 3.

TABLE 3

|   | 1. Control | 2. SA | 3. UA | 4. AMI |
|---|---|---|---|---|
| FA_16_1 | 19.9 (8.3, 58.4) | 56.6 (18.5, 85.9) | 31.3 (10.7, 61.5) | 96.2 (37.4, 133.3) |
| FA_18_0 | 7.9 (5, 58.6) | 54.1 (15.3, 68.7) | 17.2 (12.2, 49) | 39 (24.7, 46.5) |
| FA_18_1 | 129.6 (80.8, 214) | 212.1 (156.3, 286.9) | 170.9 (118.8, 258.4) | 363.5 (255.7, 518.6) |
| FA_18_2 | 112.4 (75.3, 204.4) | 206.1 (114.3, 254.8) | 161.9 (96.1, 243.2) | 308.2 (193.8, 378.8) |
| FA_22_6 | 96.9 (55.4, 157.1) | 145.3 (73.4, 189.2) | 100 (67.3, 156.3) | 232.3 (150.1, 301.4) |
| Homoserine | 5.2 (4, 6.5) | 6 (4.8, 7.2) | 5.2 (3.9, 6.8) | 9 (5.6, 16.8) |
| LPC_16_0 | 362.9 (306.8, 503.5) | 472.6 (299.6, 548.4) | 369.9 (289.2, 575.9) | 396.2 (289.1, 486.3) |
| LPC_18_0 | 112.4 (89.5, 177.2) | 158.8 (89.1, 200.3) | 111.3 (80.4, 161) | 100.1 (66.4, 135.7) |
| LPC_20_3 | 5.6 (4.5, 7.3) | 5.4 (4, 7.2) | 6.3 (4.5, 9.2) | 8.5 (5.8, 11.3) |
| LPC_20_4 | 12.3 (9.9, 16.8) | 14.9 (9.8, 18.5) | 12.7 (8.3, 18.7) | 18.5 (12.4, 31.9) |
| LPC_22_6 | 6.5 (5, 8.7) | 6.3 (4.5, 11.2) | 5.5 (4.7, 9.3) | 19.5 (5.9, 43.2) |
| MG_18_1 | 6.5 (3.7, 13) | 13.1 (4.4, 44.8) | 6.4 (3.2, 22.2) | 82.8 (36.3, 196.9) |
| PC_34_2 | 182.3 (154.2, 204.5) | 187.7 (160.3, 220.6) | 182.9 (154.1, 215.3) | 200.9 (169.5, 234.2) |
| PC_34_3 | 12.8 (9.4, 17.3) | 10.7 (7.4, 14.9) | 11.4 (8.3, 15.9) | 7.8 (5.5, 12.9) |
| SM_d18_2_16_0 | 13.4 (7.1, 19.6) | 9.2 (7.1, 14) | 13.4 (8.4, 19.6) | 12.6 (9.6, 18.4) |
| Tryptophan | 22.1 (18.3, 25.7) | 20.9 (9.1, 25.5) | 20.1 (11.1, 24.6) | 5.6 (1.9, 12) |

In Table 3, the difference between the four groups was compared by the Kruskal-Wallis test and the comparison between the two groups was analyzed by the Dwass-Steel-Critchlow-Fligner multiple comparison test. A statistical analysis result on the differences between the clinical parameters and metabolites is shown in Table 4.

TABLE 4

|   | Comparison between four groups | Control vs. SA | Control vs. UA | Control vs. AMI | SA vs. UA | AMI vs. SA | AMI vs. UA |
|---|---|---|---|---|---|---|---|
| Sex - male | <.0001 | | | | | | |
| HTN | <.0001 | | | | | | |
| DM | 0.0006 | | | | | | |
| Dyslipidemia | 0.0301 | | | | | | |
| Statin | <.0001 | | | | | | |
| Smoking | <.0001 | | | | | | |
| AGE | 0.0005 | 0.002 | 0.0038 | 0.0876 | 0.8222 | 0.9751 | 0.6974 |
| BMI | 0.0993 | 0.2115 | 0.111 | 0.6477 | 0.8576 | 0.9872 | 0.7929 |
| SBP | 0.0206 | 0.9999 | 0.8719 | 0.0294 | 0.8629 | 0.0252 | 0.2457 |
| DBP | 0.0004 | 0.0527 | 0.0639 | 0.0003 | 0.9531 | 0.2159 | 0.7302 |
| PR | 0.0081 | 0.0072 | 0.0701 | 0.5245 | 1 | 0.6262 | 0.7582 |
| WBC | 0.0004 | 0.0072 | 0.0329 | 0.0017 | 0.99 | 0.6219 | 0.8562 |
| CRP | 0.0024 | 0.4966 | 0.3516 | 0.0029 | 0.658 | 0.0183 | 0.5399 |
| Cholesterol | <.0001 | <.0001 | 0.0012 | <.0001 | 0.9992 | 0.8955 | 0.9206 |
| HDL | <.0001 | 0.0022 | <.0001 | <.0001 | 0.0873 | 0.008 | 0.9193 |
| LDL | <.0001 | 0.0142 | 0.0108 | <.0001 | 0.9981 | 0.7487 | 0.6532 |
| Triglyceride | 0.6138 | 0.9859 | 0.6961 | 0.8079 | 0.7604 | 0.8899 | 0.997 |
| AST | 0.4927 | 0.9419 | 0.885 | 0.7069 | 0.7834 | 0.8161 | 0.5717 |
| ALT | 0.6379 | 0.9559 | 0.9618 | 0.5899 | 0.9902 | 0.7613 | 0.9732 |
| Glucose | 0.0374 | 0.149 | 0.9651 | 0.1441 | 0.2457 | 0.9322 | 0.2308 |
| BUN | 0.3056 | 0.7185 | 0.2461 | 0.9914 | 0.7202 | 0.9575 | 0.5924 |
| Creatinine | 0.0004 | 0.0174 | 0.705 | 0.0006 | 0.774 | 0.1869 | 0.084 |
| HbA1c | <.0001 | 0.5614 | 0.1437 | 0.0002 | 0.0366 | <.0001 | 0.6223 |
| FA_16_1 | <.0001 | 0.0001 | 0.4619 | <.0001 | 0.294 | 0.0012 | 0.001 |
| FA_18_0 | <.0001 | <.0001 | 0.0383 | 0.0342 | 0.036 | 0.0549 | 0.486 |

TABLE 4-continued

| | Comparison between four groups | Control vs. SA | Control vs. UA | Control vs. AMI | SA vs. UA | AMI vs. SA | AMI vs. UA |
|---|---|---|---|---|---|---|---|
| FA_18_1 | <.0001 | <.0001 | 0.067 | <.0001 | 0.4952 | <.0001 | <.0001 |
| FA_18_2 | <.0001 | 0.0003 | 0.2424 | <.0001 | 0.5515 | <.0001 | <.0001 |
| FA_22_6 | <.0001 | 0.0139 | 0.8757 | <.0001 | 0.3602 | <.0001 | <.0001 |
| Homoserine | <.0001 | 0.0778 | 0.9922 | <.0001 | 0.4342 | <.0001 | <.0001 |
| LPC_16_0 | 0.0988 | 0.1058 | 0.9524 | 0.9991 | 0.9775 | 0.1431 | 0.7429 |
| LPC_18_0 | 0.0005 | 0.2124 | 0.841 | 0.0402 | 0.0868 | 0.0006 | 0.3871 |
| LPC_20_3 | <.0001 | 0.9593 | 0.4157 | <.0001 | 0.3636 | <.0001 | 0.0424 |
| LPC_20_4 | 0.0006 | 0.1804 | 0.988 | 0.0004 | 0.8016 | 0.0307 | 0.05 |
| LPC_22_6 | <.0001 | 0.9993 | 0.9023 | <.0001 | 0.9909 | <.0001 | 0.0006 |
| MG_18_1 | <.0001 | 0.0091 | 0.9878 | <.0001 | 0.29 | <.0001 | <.0001 |
| PC_34_2 | 0.037 | 0.3729 | 0.9642 | 0.0181 | 0.931 | 0.4253 | 0.3524 |
| PC_34_3 | 0.0004 | 0.0426 | 0.3933 | 0.0003 | 0.9599 | 0.153 | 0.1538 |
| SM_d18_2_16_0 | 0.0013 | 0.0263 | 0.9848 | 0.9884 | 0.031 | 0.0021 | 1 |
| Tryptophan | <.0001 | 0.2248 | 0.3619 | <.0001 | 0.9975 | <.0001 | <.0001 |

Then, a multinomial logistic regression analysis was conducted to predict the normal people and patients with stable angina, unstable angina and acute myocardial infarction. Also, the factors that can contribute to the predictor variables were extracted by the stepwise selection method. The result is shown in Table 5.

TABLE 5

| Effect | DF | Wald Chi-Square | Pr > ChiSq |
|---|---|---|---|
| HTN | 3 | 31.9507 | <.0001 |
| Statin | 3 | 29.9454 | <.0001 |
| WBC | 3 | 16.7197 | 0.0008 |
| CRP | 3 | 12.8988 | 0.0049 |
| Cholesterol | 3 | 12.6992 | 0.0053 |
| Glucose | 3 | 17.8495 | 0.0005 |
| HbA1c | 3 | 19.313 | 0.0002 |
| FA_18_0 | 3 | 19.2558 | 0.0002 |
| FA_22_6 | 3 | 15.8434 | 0.0012 |
| Homoserine | 3 | 25.0439 | <.0001 |
| LPC_16_0 | 3 | 13.0378 | 0.0046 |
| LPC_18_0 | 3 | 24.7024 | <.0001 |
| LPC_20_4 | 3 | 15.2679 | 0.0016 |
| LPC_22_6 | 3 | 20.0364 | 0.0002 |
| PC_34_2 | 3 | 21.206 | <.0001 |
| Tryptophan | 3 | 16.8012 | 0.0008 |

Diagnostic yield of each group was predicted using the factors described in Table 5 and the following model. The constants used in the following model were calculated by analysis of maximum likelihood estimates. The predictive equations obtained for the disease groups are as follows.

Probability of onset of stable angina (SA), [Equation 1]

$$P_{sa} = \pi_1(\chi) = \frac{\exp(\alpha_1 + \beta'_1 \chi)}{1 + \exp(\alpha_1 + \beta'_1 \chi) + \exp(\alpha_2 + \beta'_2 \chi) + \exp(\alpha_3 + \beta'_3 \chi)}$$

Probability of onset of acute myocardial infarction (AMI), [Equation 2]

$$P_{ami} = \pi_3(\chi) = \frac{\exp(\alpha_3 + \beta'_3 \chi)}{1 + \exp(\alpha_1 + \beta'_1 \chi) + \exp(\alpha_2 + \beta'_2 \chi) + \exp(\alpha_3 + \beta'_3 \chi)}$$

Probability of onset of unstable angina (UA), [Equation 3]

$$(P_{ua}) = \pi_2(\chi) = \frac{\exp(\alpha_2 + \beta'_2 \chi)}{1 + \exp(\alpha_1 + \beta'_1 \chi) + \exp(\alpha_2 + \beta'_2 \chi) + \exp(\alpha_3 + \beta'_3 \chi)}$$

$\alpha_1 = -5.1033$,
$\alpha_2 = -7.2726$,
$\alpha_3 = -16.5253$,
$\beta'_{1\chi} = 3.233*HTN + 3.016*statin + 0.4336*WBC - 0.0364*CRP - 0.0189*cholesterol + 0.0534*glucose - 0.8651*HbA1c + 0.0689*FA\_18\_0 - 0.00252*FA\_22\_6 + 0.0332*homoserine - 0.0037*LPC\_16\_0 + 0.00318*LPC\_18\_0 - 0.0209*LPC\_20\_4 + 0.1109*LPC\_22\_6 + 0.0118*PC\_34\_2 - 0.0159*tryptophan$,
$\beta'_{2\chi} = 3.18*HTN + 1.4578*statin + 0.4631*WBC - 0.00977*CRP - 0.02*cholesterol + 0.0127*glucose + 0.0981*HbA1c + 0.0349*FA\_18\_0 - 0.0173*FA\_22\_6 + 0.0564*homoserine + 0.00993*LPC\_16\_0 - 0.0308*LPC\_18\_0 - 0.1525*LPC\_20\_4 + 0.2896*LPC\_22\_6 + 0.0239*PC\_34\_2 + 0.00366*tryptophan$,
$\beta'_{3\chi} = 3.9577*HTN - 1.6837*statin + 0.5634*WBC + 0.0705*CRP - 0.00031*cholesterol + 0.0174*glucose + 0.3797*HbA1c - 0.00059*FA\_18\_0 + 0.00472*FA\_22\_6 + 0.6163*homoserine - 0.00314*LPC\_16\_0 - 0.0438*LPC\_18\_0 - 0.0411*LPC\_20\_4 + 0.2548*LPC\_22\_6 + 0.0517*PC\_34\_2 - 0.2288*tryptophan$.

As a result, the accuracy of prediction was calculated as 81.31%, 69.57%, 44.83% and 84.48% for the normal (control), stable angina (SA), unstable angina (UA) and myocardial infarction (AMI) groups, respectively. This means that acute myocardial infarction and stable angina can be distinguishably diagnosed and the possibility of the onset thereof can be predicted using the biological metabolites and clinical parameters according to the present disclosure and the above equations. A result of the statistical analysis is shown in Table 6.

TABLE 6

| Observed values | | Predicted values | | | | |
|---|---|---|---|---|---|---|
| | | Control | SA | UA | AMI | Total |
| 1. Control | Number | 87 | 12 | 2 | 0 | 101 |
| | Prediction accuracy (%) | 86.14 | 11.88 | 1.98 | 0.00 | 100.00 |

TABLE 6-continued

| Observed values | | Predicted values | | | | |
|---|---|---|---|---|---|---|
| | | Control | SA | UA | AMI | Total |
| 2. SA | Number | 12 | 80 | 12 | 3 | 107 |
| | Prediction accuracy (%) | 11.21 | 74.77 | 11.21 | 2.80 | 100.00 |
| 3. UA | Number | 7 | 19 | 13 | 6 | 45 |
| | Prediction accuracy (%) | 15.56 | 42.22 | 28.89 | 13.33 | 100.00 |
| 4. AMI | Number | 1 | 4 | 2 | 49 | 56 |
| | Prediction accuracy (%) | 1.79 | 7.14 | 3.57 | 87.50 | 100.00 |
| Total | | 107 | 115 | 29 | 58 | 309 |

What is claimed is:

1. A method for diagnosis of coronary heart disease (CHD), comprising:

obtaining a blood sample from a patient;

deproteinizing said blood sample by pretreating with methanol;

detecting the levels of metabolites of said deproteinized blood sample, said metabolites comprising tryptophan, homoserine, fatty acid (18:0) (FA_18_0), fatty acid (22:6) (FA_22_6), lysophosphatidylcholine (lysoPC) (16:0) (LPC_16_0), lysoPC (18:0) (LPC_18_0), lysoPC (20:4) (LPC_20_4), lysoPC (22:6) (LPC_22_6) and phosphatidylcholine (PC) (34:2) (PC_34_2);

analyzing said levels of metabolites and clinical parameters of said deproteinized blood sample, said clinical parameters comprising a white blood cell (WBC), a C-reactive protein (CRP), cholesterol, glucose and hemoglobin A1c (HbA1c), wherein analyzing comprises performing liquid chromatography-mass spectrometry for the blood sample, obtaining chromatograms and mass spectrometry data from the result of the mass spectrometry, and obtaining normalized peak areas by dividing the peak areas of the mass spectrometry data by the total peak of the chromatogram, and the normalized peak areas of the respective metabolites are substituted in Equation 1 or 2;

Probability of onset of stable angina (SA), [Equation 1]

$$P_{sa} = \pi_1(\chi) = \frac{\exp(\alpha_1 + \beta'_1 \chi)}{1 + \exp(\alpha_1 + \beta'_1 \chi) + \exp(\alpha_2 + \beta'_2 \chi) + \exp(\alpha_3 + \beta'_3 \chi)}$$

Probability of onset of acute myocardial infarction (AMI), [Equation 2]

$$P_{ami} = \pi_3(\chi) = \frac{\exp(\alpha_3 + \beta'_3 \chi)}{1 + \exp(\alpha_1 + \beta'_1 \chi) + \exp(\alpha_2 + \beta'_2 \chi) + \exp(\alpha_3 + \beta'_3 \chi)}$$

wherein $\alpha_1 = -5.1033$, $\alpha_2 = -7.2726$, $\alpha_3 = -16.5253$, $\beta'_{1\chi} = 3.233*HTN+3.016*statin+0.4336*WBC-0.0364*CRP-0.0189*cholesterol+0.0534*glucose-0.8651*HbA1c+0.0689*FA\_18\_0-0.00252*FA\_22\_6+0.0332*homoserine-0.0037*LPC\_16\_0+0.00318*LPC\_18\_0-0.0209*LPC\_20\_4+0.1109*LPC\_22\_6+0.0118*PC\_34\_2-0.0159*tryptophan$, $\beta'_{2\chi} = 3.18*HTN+1.4578*statin+0.4631*WBC-0.00977*CRP-0.02*cholesterol+0.0127*glucose+0.0981*HbA1c+0.0349*FA\_18\_0-0.0173*FA\_22\_6+0.0564*homoserine+0.00993*LPC\_16\_0-0.0308*LPC\_18\_0-0.1525*LPC\_20\_4+0.2896*LPC\_22\_6+0.0239*PC\_34\_2+0.00366*tryptophan$, $\beta'_{3\chi} = 3.9577*HTN-1.6837*statin+0.5634*WBC+0.0705*CRP-0.00031*cholesterol+0.0174*glucose+0.3797*HbA1c-0.00059*FA\_18\_0+0.00472*FA\_22\_6+0.6163*homoserine-0.00314*LPC\_16\_0-0.0438*LPC\_18\_0-0.0411*LPC\_20\_4+0.2548*LPC\_22\_6+0.0517*PC\_34\_2-0.2288*tryptophan$, checking the presence of hypertension (HTN) and medication of statin of the subject; and predicting stable angina (SA) and acute myocardial infarction (AMI) by substituting the blood levels of the metabolites and clinical parameters contained in the blood sample, the presence of hypertension and the medication of statin in Equation 1 or 2, wherein the unit of the blood levels of the clinical parameters of the subject substituted in Equation 1 or 2 are cell/mm$^3$ for the white blood cell (WBC), mg/L for the C-reactive protein (CRP), mg/dL for the cholesterol, mg/dL for the glucose and % for the hemoglobin A1c (HbA1c), and for the presence of hypertension (HTN), 1 is substituted in Equation 1 or 2 when the systolic blood pressure of the subject is 140 mmHg or higher or the diastolic blood pressure is 90 mmHg or higher and 0 is substituted when the systolic blood pressure is below 140 mmHg and, for the medication of statin, 1 is substituted in Equation 1 or 2 when the subject takes statin and 0 is substituted when the subject does not take statin.

* * * * *